US008612014B2

(12) United States Patent
Rahman et al.

(10) Patent No.: US 8,612,014 B2
(45) Date of Patent: *Dec. 17, 2013

(54) MULTIPLE TELEMETRY AND/OR CHARGING COIL CONFIGURATIONS FOR AN IMPLANTABLE MEDICAL DEVICE SYSTEM

(71) Applicant: Boston Scientific Neuromodulation Corporation, Valencia, CA (US)

(72) Inventors: Md. Mizanur Rahman, Stevenson Ranch, CA (US); Daniel Joseph Klostermann, Valencia, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 13/768,893

(22) Filed: Feb. 15, 2013

(65) Prior Publication Data

US 2013/0165995 A1 Jun. 27, 2013

Related U.S. Application Data

(63) Continuation of application No. 13/423,954, filed on Mar. 19, 2012, now Pat. No. 8,391,991, which is a continuation of application No. 13/206,622, filed on Aug. 10, 2011, now Pat. No. 8,175,716, which is a continuation of application No. 11/622,395, filed on Jan. 11, 2007, now Pat. No. 8,010,205.

(51) Int. Cl.
*A61N 1/00* (2006.01)

(52) U.S. Cl.
USPC ........................................... 607/60

(58) Field of Classification Search
USPC ....................................................... 607/61, 60
See application file for complete search history.

(56) References Cited

U.S. PATENT DOCUMENTS

| 5,630,835 | A | 5/1997 | Brownlee |
| 5,741,316 | A | 4/1998 | Chen et al. |
| 5,843,139 | A | 12/1998 | Goedeke et al. |
| 5,991,664 | A | 11/1999 | Seligman |
| 6,047,214 | A | 4/2000 | Mueller et al. |
| 6,115,636 | A | 9/2000 | Ryan |
| 6,169,925 | B1 | 1/2001 | Villaseca et al. |

(Continued)

FOREIGN PATENT DOCUMENTS

WO 2006/010013 1/2006

*Primary Examiner* — George Manuel
*Assistant Examiner* — Robert N Wieland
(74) *Attorney, Agent, or Firm* — Wong, Cabello, Lutsch, Rutherford & Brucculeri, LLP

(57) ABSTRACT

An implantable medical device system for orientation-independent telemetry to and from the device are disclosed. The system includes an external controller which produces an electromagnetic field to induce a current in a coil in the implantable medical device and vise versa. In a preferred embodiment, the external controller comprises three orthogonal coils, each of which is potentially activated to generate or receive the electromagnetic field. Algorithms are disclosed to allow for the choice of one or more of the coils best suited for telemetry based on the chosen coil's orientation with respect to the telemetry coil in the implantable medical device. Because all three of the orthogonal coils are potentially activated if necessary, the result is that at least one of the coils will be in a proper orientation with respect to the coil in the implantable medical device, thereby improving telemetry or power transfer efficiency.

17 Claims, 10 Drawing Sheets

(56) References Cited

U.S. PATENT DOCUMENTS

| | | |
|---|---|---|
| 6,298,271 B1 | 10/2001 | Weijand |
| 6,345,203 B1 | 2/2002 | Mueller et al. |
| 6,366,817 B1 | 4/2002 | Kung |
| 6,430,444 B1 | 8/2002 | Borza |
| 6,450,953 B1 | 9/2002 | Place et al. |
| 6,463,329 B1 | 10/2002 | Goedeke |
| 6,516,227 B1 | 2/2003 | Meadows et al. |
| 6,526,310 B1 | 2/2003 | Carter et al. |
| 7,281,314 B2 | 10/2007 | Hess et al. |
| 7,444,181 B2 | 10/2008 | Shi et al. |
| 7,546,165 B2 | 6/2009 | Zarembo et al. |
| 7,650,192 B2 | 1/2010 | Wahlstrand |
| 7,672,731 B2 | 3/2010 | Dublin et al. |
| 7,925,356 B2 | 4/2011 | Li et al. |
| 2002/0151770 A1 | 10/2002 | Noll et al. |
| 2005/0228259 A1 | 10/2005 | Glukhovsky et al. |
| 2006/0142820 A1 | 6/2006 | Von Arx et al. |
| 2006/0195162 A1 | 8/2006 | Von Arx et al. |
| 2007/0270660 A1 | 11/2007 | Caylor et al. |
| 2008/0234784 A1* | 9/2008 | Li et al. .................. 607/60 |
| 2010/0114253 A1 | 5/2010 | Wahlstrand |

* cited by examiner

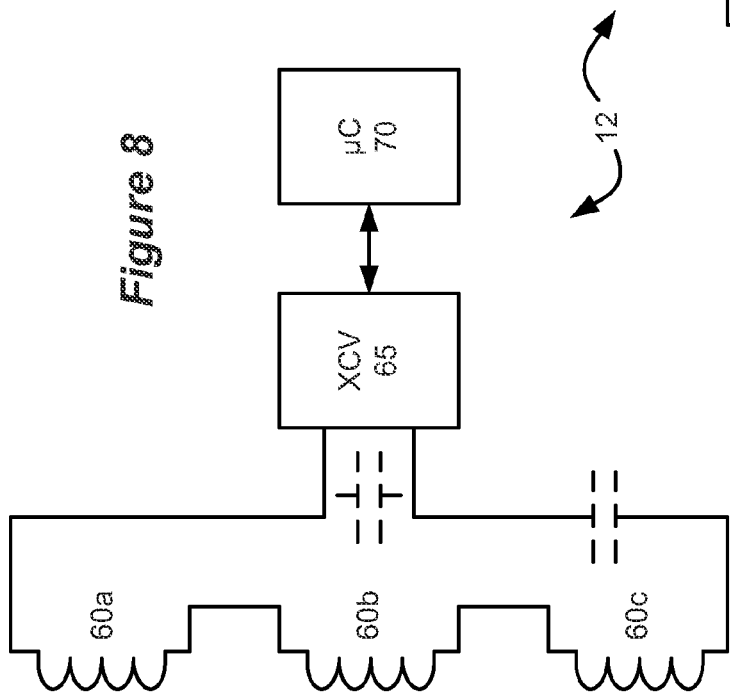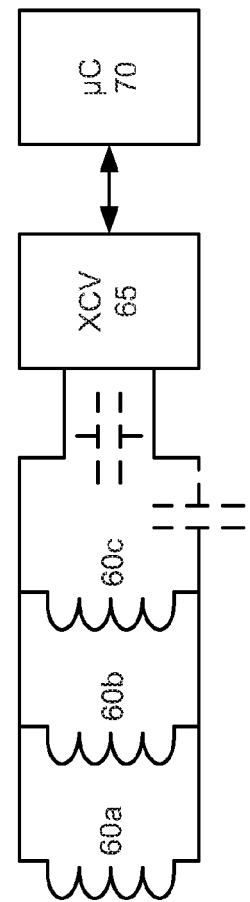

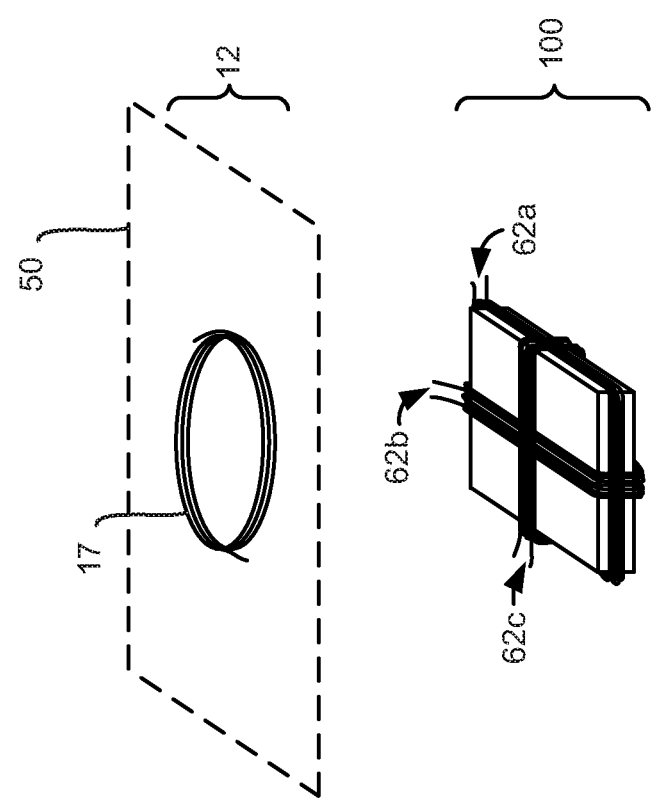

MULTIPLE TELEMETRY AND/OR CHARGING COIL CONFIGURATIONS FOR AN IMPLANTABLE MEDICAL DEVICE SYSTEM

CROSS REFERENCE TO RELATED APPLICATIONS

This is a continuation of U.S. patent application Ser. No. 13/423,954, filed Mar. 9, 2012 (now U.S. Pat. No. 8,391,991), which is a continuation of U.S. patent application Ser. No. 13/206,622, filed Aug. 10, 2011 (now U.S. Pat. No. 8,175, 716), which is a continuation of U.S. patent application Ser. No. 11/622,395 filed Jan. 11, 2007 (now U.S. Pat. No. 8,010, 205). Priority is claimed to these applications, and they are incorporated herein by reference in their entireties.

FIELD OF THE INVENTION

The present invention relates generally to implantable medical devices, and more particularly, to a system for providing telemetry to an implantable medical device from an external controller.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a Spinal Cord Stimulation (SCS) system, such as that disclosed in U.S. Pat. No. 6,516,227, which is incorporated herein by reference in its entirety.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. The signal wires 112 and 114 are connected to the IPG 100 by way of an interface 115, which may be any suitable device that allows the leads 102 and 104 (or a lead extension, not shown) to be removably connected to the IPG 100. Interface 115 may comprise, for example, an electromechanical connector arrangement including lead connectors 38a and 38b configured to mate with corresponding connectors 119a and 119b on the leads 102 and 104. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from an external controller 12 as explained further below, and a charging coil 18 for charging or recharging the IPG's power source or battery 26 using an external charger (not shown). A feedthrough assembly 24 routes the various electrode signals from the electronic substrate assembly 14 to the lead connectors 38a, 38b, which are in turn coupled to the leads 102 and 104 (see FIGS. 1A and 1B). The IPG 100 further comprises a header connector 36, which among other things houses the lead connectors 38a, 38b. The IPG 100 can further include a telemetry antenna or coil 13 (discussed further below) for receipt and transmission of data to an external device such as a hand-held or clinician programmer (not shown), which can be mounted within the header connector 36. As already mentioned, the IPG 100 usually also includes a power source, and in particular a rechargeable battery 26.

Further details concerning the structure and function of typical IPGs and IPG systems are disclosed in U.S. patent application Ser. No. 11/305,898, filed Dec. 14, 2005, which is filed herewith via an information disclosure statement and which is incorporated herein by reference.

As one can appreciate, IPGs require programming data to function as required for a given patient. Typically, such programming data is wirelessly telemetered into the IPG 100 from the external controller 12. An exemplary external controller 12 is typically flat and fits in a patient's or clinician's hand for easy portable use in programming the IPG 100.

Wireless data telemetry between the IPG 100 and the external controller 12 is typically based on magnetic induction, and so requires telemetry coil 17 in the external controller 12 and telemetry coil 13 the IPG 100. When data is to be sent from the external controller 12 to the IPG 100, coil 17 is energized with alternating current (AC), which induces an electromagnetic field, which in turn induces a current in the IPG's telemetry coil 13. The power used to energize the coil 17 can come from a battery or batteries in the external controller (not shown), from a wall outlet via a plug (not shown), etc. The induced current can then be transformed at the IPG 100 back into the telemetered data signals. To improve the magnetic flux density, and hence the efficiency of the energy transfer, the IPG's telemetry coil 13 may be wrapped around a ferrite core 13'. As is well known, inductive transmission of data from coil 17 to coil 13 can occur transcutaneously, i.e., through the patient's tissue 25.

Optimally, IPG systems are simple enough that a patient or clinician can use the external controller 12 without medical supervision. This usually requires instruction on how to best use the external controller 12 in relation to the implanted IPG 100. Because the external controller 12 and IPG 100 are typically both flat, users are told that telemetry will be most efficient and effective when the distance between the external controller 12 and the IPG 100 is minimized; when the planes of these two devices are parallel; and when the devices "overlap" one another through the patient's tissue 25. Such instruction results from an understanding of the electromagnetic interaction of the coils 17 and 13, which is shown in FIG. 3. Shown is the optimal orientation of the two coils 17, 13 with respect to each other, with both coils lying in planes 50, 52 parallel to each other, and with the axis of both coils 54, 56 being colinear. When such an ideal condition is met, and assuming the distance D between the two coils is also minimized, energy transfer from coil 17 in the external controller 12 to coil 13 in the IPG 100 will be maximized.

However, realization of this ideal condition necessarily relies on successful implementation by the user of the external controller 12. For example, and as shown in FIG. 4, if the angle θ between the axis 54 of coil 17 and the axis 56 of coil 13 is non-ideal (i.e., non-zero), energy transfer will be non-ideal, which means that data may not be telemetered. When the axes 54, 56, are perpendicular, theoretically no energy will be transferred, and realistically only a negligible amount of energy will be transferred. Another non-ideal orientation between coil 17 and coil 13 is shown in FIG. 5. In this instance, the axes 54 and 56 of the coils are parallel, as are their planes 50 and 52, but they are not colinear, with the result that the coils are not overlapping. This too adversely impacts energy transfer from coil 17 to coil 13.

The non-ideal orientations depicted in FIGS. 4 and 5 illustrate that a user of an external controller 12 must be attentive to proper placement of the controller 12 relative to the IPG 100 and to the instructions noted earlier. Requiring correct implementation by the user is of course a drawback of such traditional IPG system hardware, because it is unrealistic to assume that any given user will be so attentive, and as a result data telemetry may be adversely affected.

Further exacerbating the potential problem of improper external controller-to-IPG orientation is the recognition that such an improper orientation is not necessarily always the result of user inadvertence. It has so far been assumed that it is relatively easy for the user to understand or infer the positioning of the coils 17 and 13. For example, when both the external controller 12 and the IPG 100 are basically flat, placing the coils 17, 13 close to the ideal orientation depicted in FIG. 3 is not difficult. But what if the external controller 12 or IPG 100 is not flat? What if the coils are mounted inside the housings in a manner in which the coil position cannot be inferred? What if the IPG 100 is implanted deep within a patient, such that the orientation of its coil 13 cannot be inferred through the patient's tissue? What if the IPG 100 moves or rotates within the patient after it is implanted? Any of these effects can make it difficult or impossible for even an attentive user to properly align the coil 17 in the external controller 12 and the coil 13 in the IPG 100.

An improved solution to this coil alignment problem would be one in which proper alignment between the external controller 12 and the IPG 100 could be reasonably assured, independent of their relative orientations. This disclosure provides embodiments of such a solution.

BRIEF DESCRIPTION OF THE DRAWINGS

FIGS. 8 and 9 show examples of the circuitry used to simultaneously stimulate the three orthogonal coils, where the figures respectively show the coils in serial and parallel configurations.

FIG. 13 shows an alternative embodiment of the invention in which the three orthogonal telemetry coils are provided in the IPG.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

The description that follows relates to use of the invention within a spinal cord stimulation (SCS) system. However, it is to be understood that the invention is not so limited. Rather, the invention may be used with any type of implantable medical device system that could benefit from improved techniques for providing orientation independence between an external controller and the device. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

Figure 3:
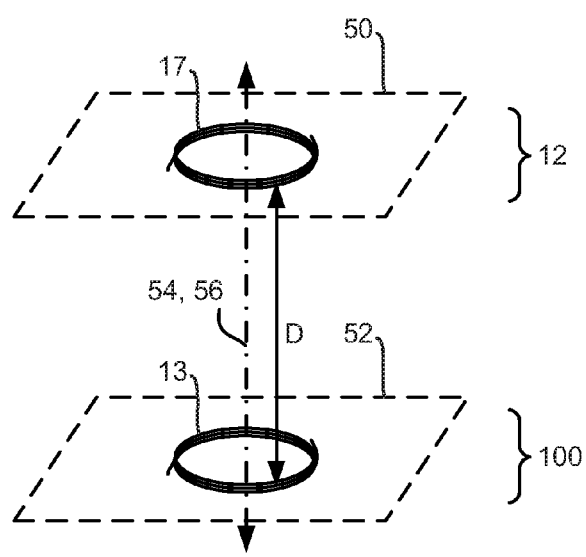
FIG. 3 shows an ideal orientation between the telemetry coils in the IPG and the external controller to maximize energy transfer.
Figure 4:
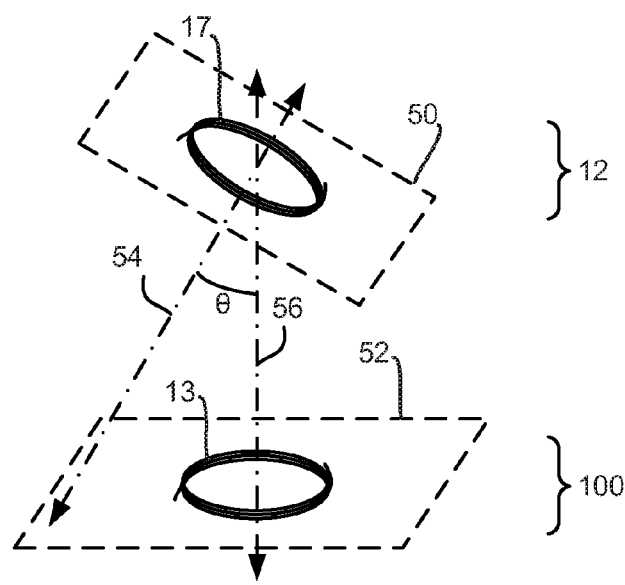
FIGS. 4 and 5 show non-ideal orientation between the telemetry coils in the IPG and the external controller.
Figure 5:
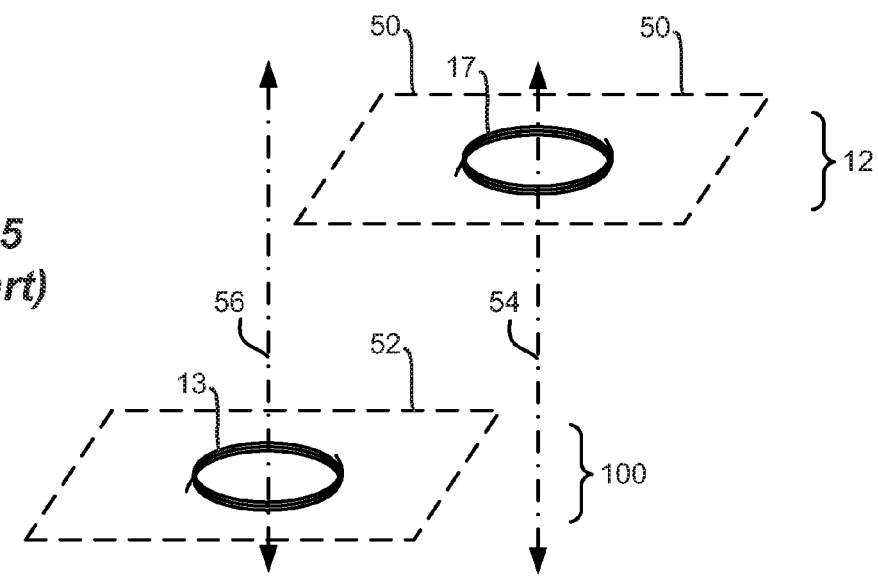
Figure 6:
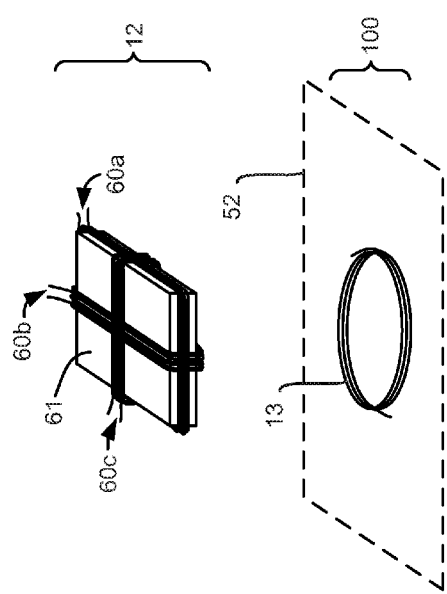
FIG. 6 shows an embodiment of the invention in which three orthogonal telemetry coils are provided in the external controller.

Embodiments of an improved IPG system for orientation-independent telemetry in an IPG are disclosed. As shown in FIG. 6, an embodiment of the solution proposed herein replaces the single coil 17 in the external controller 12 (see FIG. 3-5) with three orthogonal telemetry coils 60*a-c*, each of which is potentially energized by the external controller 12 as explained further below. Because all three of the coils 60*a-c* are potentially energized if necessary, the result is that at least one of the coils 60*a-c* will be sufficiently parallel with the plane 52 of the telemetry coil 13 in the IPG 100, to allow for suitable data telemetry. At a minimum, no orientation of the external controller 12 with respect to the IPG 100 will result in a condition in which an insignificant amount of electromagnetic energy 29 is transferred between the controller coils 60*a-c* and the IPG's coil 13.

Figure 7:
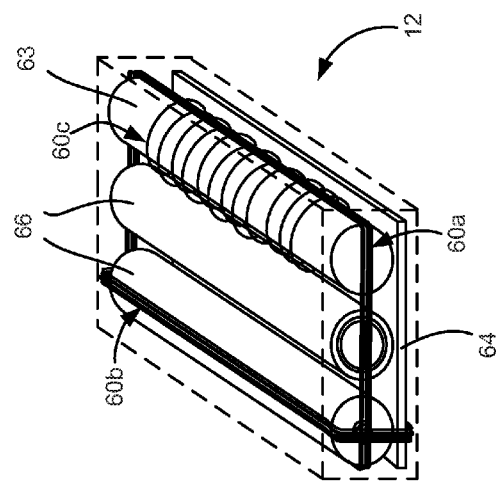
FIG. 7 shows an embodiment of the external controller having three orthogonal telemetry coils in which the coils are wound around or integrated with various electronic components in the external controller.

In FIG. 6, the three orthogonal coils 60*a-c* are shown as wrapped around a block 61. This block 61 can comprise a ferrite core, which, as noted earlier, increases the magnetic flux density to increase the energy 29 transfer between the coils 60*a-c* and the IPG coil 13. Alternatively, block 61 can comprise other structures or materials, or could represent an air core. Furthermore, as shown in FIG. 7, the coils 60*a-c* can be wound around or integrated with various electronic components in the external controller 12. Thus, as shown, the external controller 12 comprises a printed circuit board 64, which can include the various circuitry such as a microcontroller, a transceiver and switching circuitry (to be discussed in further detail below), etc. Batteries 66 are also shown, which provide power to the printed circuit board 64 and its associated circuitry. Also shown is a ferrite core 63, which as just noted is helpful in increasing magnetic flux density. As shown, the three telemetry coils 60a-c are wound around these components in various manners such that their axes are orthogonal, just as they are shown in FIG. 6. While FIG. 7 illustrates one way of winding the coils 60a-c around the various components in the external controller 12, such coils can be wound in any myriad of ways to the same beneficial end of creating an external controller which is largely orientation-independent with respect to the IPG 100.

FIGS. 8 and 9 show examples of the circuitry in the external controller 12 used to simultaneously stimulate the three orthogonal coils 60a-c, and respectively show the coils in serial and parallel configurations. As is typical, the coils 60a-c are coupled to transceiver (XCV) circuitry 65, which is controlled by a microcontroller 70. Because the coils 60a-c may be used to receive information communicated back from the IPG 100, transceiver (i.e., transmitter and receiver) circuitry 65 is preferred. However, if the coils 60a-c are used exclusively for providing energy 29 to the receiving coil 13 in the IPG 100 without also receiving any back telemetry from the IPG 100, then only transmitter circuitry 65 would be necessary in the external controller 12. The microcontroller 70, as well as controlling the transceiver circuitry 65, controls other aspects of the external controller 12, such as charging of its batteries 66 (see FIG. 7), receiving and processing user inputs such as various button presses (not shown), providing indications to user regarding the status of telemetry, etc.

Because the magnetic field emitted by the telemetry coils 60a-c is AC (alternating current), the coils 60a-c are made to resonate as an LC circuit, as is well known. The capacitance necessary for such resonance can be positioned in parallel with the coils, or in series with the coils, both of which are shown in dotted lines in the figures. For the field to resonate with an appropriate frequency or within an appropriate frequency band, it is necessary to tune the inductance of the coils and/or the capacitance(s), again, as is well known.

In the embodiments of FIGS. 8 and 9, all three coils 60a-c are energized simultaneously, with the effect that three generally perpendicular fields are produced for receipt by the IPG's telemetry coil 13. While suitable in some applications, it should be noted that simultaneously-stimulated coils may have drawbacks. For example, it may be more difficult to simultaneously tune the resonance of the coils. Also, because each of the coils 60a-c will produce a field, those orthogonal fields may interfere with one another such that nulls might be present at some points in the overall field produced. However, these effects can be minimized by simulation and modeling. Furthermore, the approach of FIGS. 8 and 9 will necessarily require energizing all of the coils 60a-c, even if a given coil does not significantly contribute to telemetry, e.g., because the axis of that coil is perpendicular to the axis 56 of the IPG coil 13 (see, e.g., FIG. 4).

Figure 11:
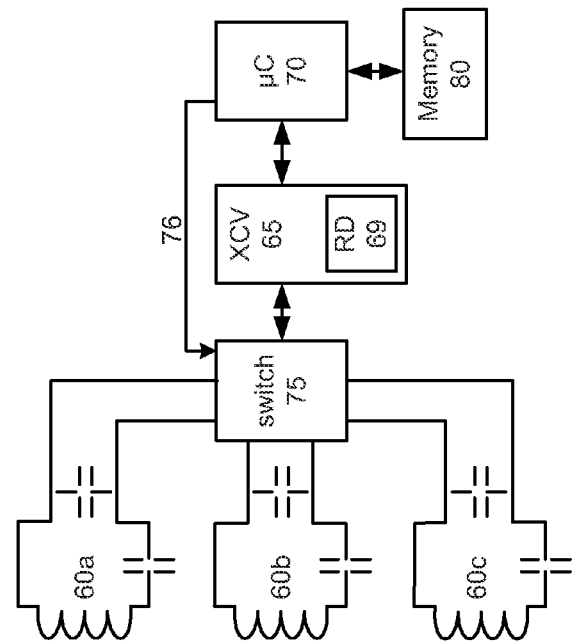
FIGS. 10 and 11 show examples of the circuitry used to independently stimulate the three orthogonal coils.
Figure 10:
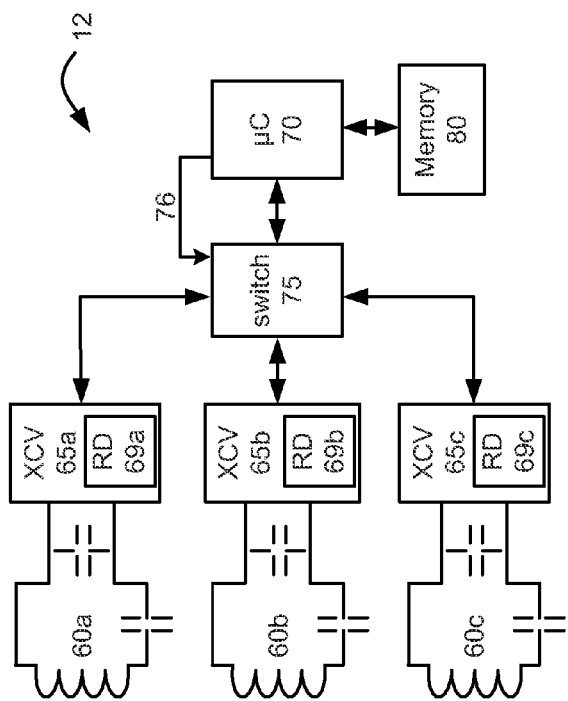

Because of these concerns or potential inefficiencies, in the preferred implementation of the invention, the orthogonal telemetry coils 60a-c are independently and individually energized, such as through use of the circuitry of FIGS. 10 and 11. As seen in those circuits, a switch 75 is provided for establishing control of a single of the coils 60a-c at any given time. The switch 75 can either be placed between the microcontroller 70 and the transceivers 65a-c for each of the coils 60a-c (FIG. 10) or can be placed between a single transceiver 65 and the coils 60a-c (FIG. 11). Although it requires multiple transceiver circuits 65a-c, the approach of FIG. 10 provides better flexibility, as it allows each coil 60/transceiver 65 pair to be individually tuned. In either version of the external controller circuitry, a switching signal 76 from the microcontroller 70 indicates to the switch 75 which of the coils 60a-c is presently used.

Regardless of the embodiment used for the external controller circuitry (either FIG. 10 or 11), such circuitry can be used in many different ways to establish telemetry with a given IPG 100. For example, according to a very simple protocol, each of the telemetry coils can be sequentially activated (60a, then 60b, then 60c, then 60a, etc.), with each coil 60a-c sending the same portion of programming data. As noted before, because at least one of the coils 60a-c would have an appropriate orientation vis-à-vis the IPG coil 13, satisfactory telemetry would be accomplished. But such sequential coil activation, while simple to implement, is potentially wasteful of time, and of the external controller 12's power, because it is likely that at least one of the coils 60a-60c is not making a significant contribution to telemetry.

Figure 12A:
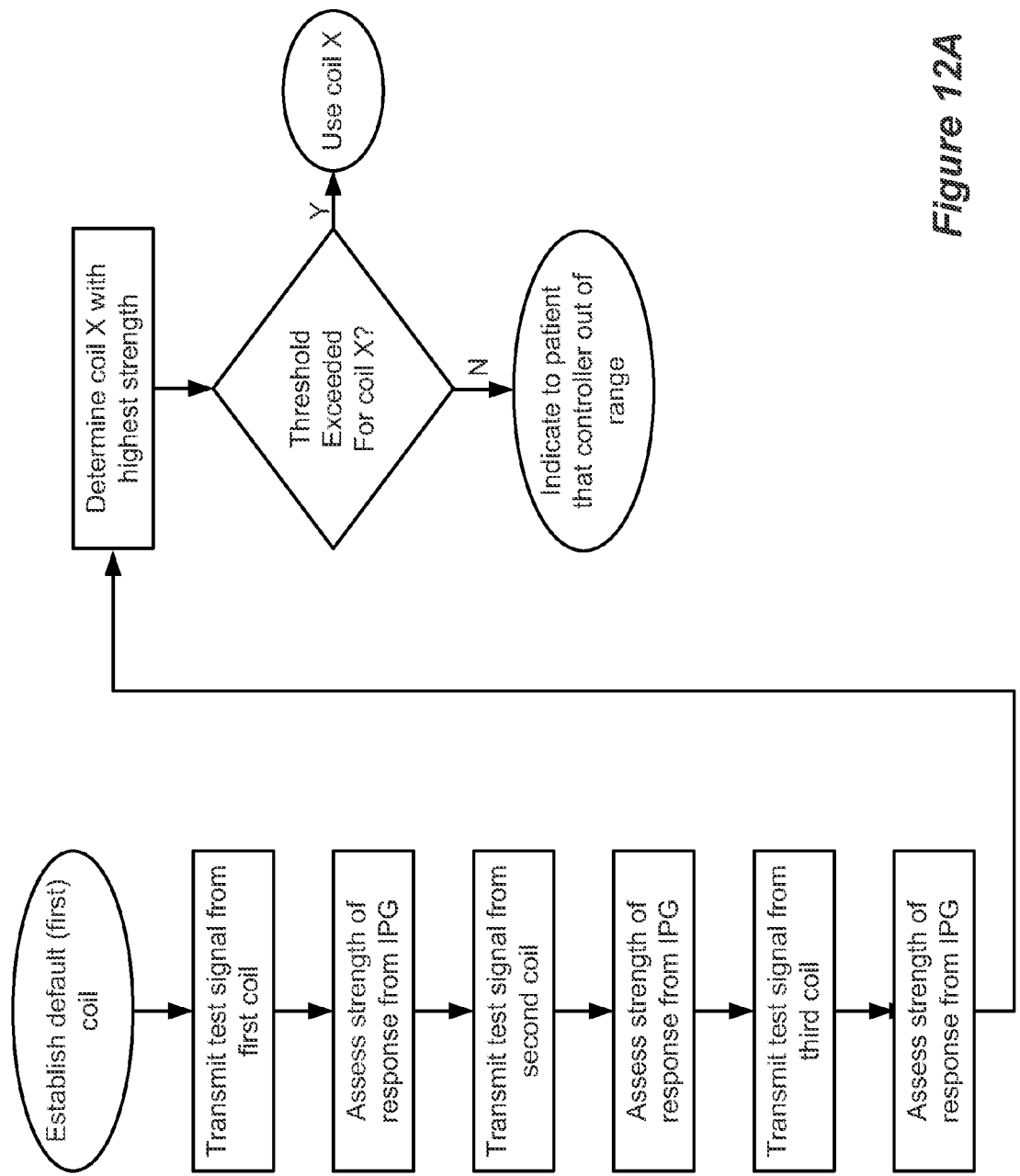
FIGS. 12A and 12B show algorithms useable with embodiments of the invention for choosing one of the three orthogonal coils as the coil to be used during telemetry.
Figure 12B:
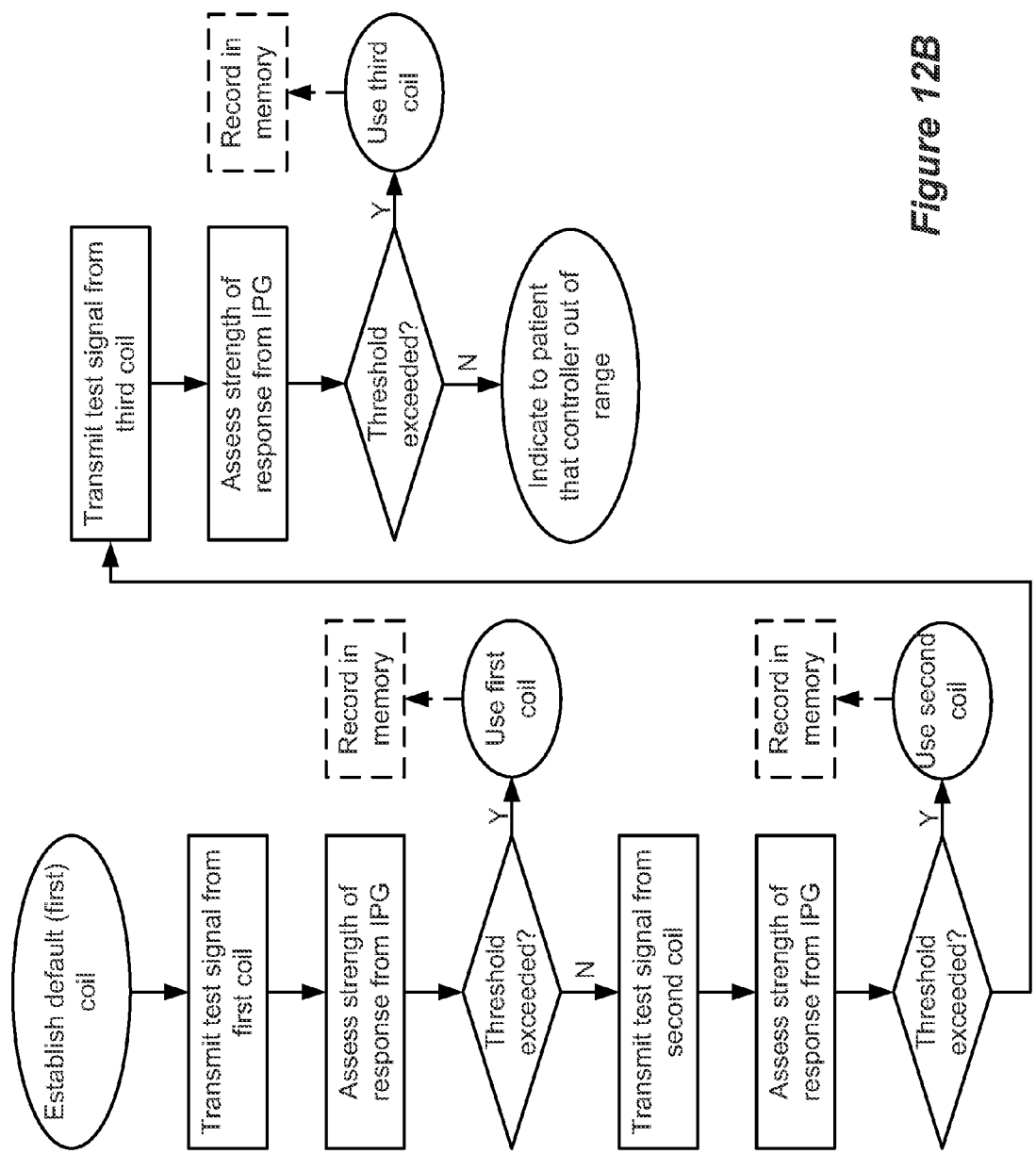

Accordingly, the external controller circuitry of FIG. 10 or 11 is preferably used in accordance with an algorithm that selects the most ideal of the coils 60a-c as the one to be used during telemetry to the IPG. FIGS. 12A and 12B illustrate exemplary algorithms useful in this regard. One skilled in the art will realize that these algorithms are easily implemented using the microcontroller 70 in the external controller 12. The algorithms as depicted in flow chart form are self-explanatory, and so are not belabored here.

Both algorithms rely on sending test signals from the external controller 12 to the IPG 100 prior to beginning actual telemetry to assess the transmission efficiency of each of the telemetry coils 60a-c. These test signals are sent from one of the coils 60a-c in the external controller 12. After sending the test signal, the external controller 12 waits for an acknowledgment response from the IPG 100 and assesses the signal strength of that response using the particular sending coil as the receiving antenna. In that regard, the circuitry in the external controller 12 contains one or more reception detectors (RD) 69 (FIGS. 10 and 11) for assessing the signal strength of the received acknowledgment signal, which can occur in numerous places in the circuitry, but which is most logically associated with the transceiver circuit(s) 65. Reception detection of this type is known in the art of implantable medical device systems, and thus such details are not discussed here.

The main difference between the two algorithms depicted in FIGS. 12A and 12B is whether all coils 60a-c are necessarily tested. In the algorithm of 12A, all coils 60a, 60b, and 60c are sequentially used to send a test signal, and the signal strength of the acknowledgement response is assessed for each. The coil with the highest received signal strength (coil X) is provisionally chosen as the coil to be used during telemetry, although to ensure that this coil is acceptable, the signal strength is compared against a pre-set threshold chosen to ensure suitable transmission efficiency. If the signal strength of the received response at coil X exceeds the threshold, then coil X is thereafter chosen as the optimal coil for telemetry, and telemetry can thereafter commence using coil X. If the signal strength of the received response at coil X does not exceed the threshold, then the external controller 12 indicates to the patient that the controller 12 is not properly located. Such indication can occur for example by lighting an appropriate LED on the case of the external controller 12, or by providing a message in text or an icon on a display such as a LCD as is well known.

The algorithm of FIG. 12B is similar, but does not bother to check the transmission efficiency of subsequent telemetry coils 60a-c if a suitable coil has been determined. Thus, like the algorithm of FIG. 12A, the algorithm of FIG. 12B sends a test signal from a first coil (e.g., 60a) and assesses the strength of the response back at coil 60a. If the response received at the first coil exceeds the threshold, then the first coil is thereafter chosen as the optimal, and telemetry can thereafter commence using the first coil. If the threshold is not exceeded, then the second coil (e.g., 60b) is assessed, and if it is acceptable, it is chosen. Otherwise the third coil (e.g., 60c) is assessed, etc., until such time as either the third coil is deemed acceptable as the telemetry coil of choice, or the user of the external controller 12 is notified of the out-of-position condition as explained above. In short, the algorithm of FIG. 12B does not necessarily assess each of the coils 60a-c, but instead stops when a suitable coil is determined.

A preferred first step in each algorithm, and particularly in the algorithm of FIG. 12B, is to establish a default coil which is assessed first. For example, consider an external controller 12 having a basic flat shape such as is shown in FIG. 6. Assuming the user attempts to use such an external controller 12 as expected, it would be expected that coil 60a would have the most efficient orientation with respect to the coil 13 in the IPG 100. Accordingly, it is sensible to check this coil 60a first, because if the algorithm of FIG. 12B is used, it will likely result that coil 60a is chosen as acceptable, and time and energy will not be spent to assess coils 60b and 60c. While 60a might be the preferred default coil, a secondary preferred coil (e.g., either 60b or 60c) can be automatically assessed as the next in line.

The default coil to be used (or, more generally, the order in which the coils will be assessed) can also be established based on historical results. For example, if history shows that transmission coil 60b has the highest response signal strength 90% of the time, and that coil 60c has the highest response signal strength 9% of the time, coil 60b can be used as the default, followed by coil 60c, and coil 60a. Such history can be stored the in ancillary steps shown in dotted lines in FIG. 12B. As shown, when a particular coil is determined to be optimal for telemetry, that fact is recorded in a memory 80 associated with the microcontroller 70 (FIGS. 10 and 11). Thus, when the algorithm of FIG. 12B starts, this past history in memory 80 can be queried to determine the most logical order for assessment of the various coils 60a-c.

In each of the algorithms illustrated in FIGS. 12A and 12B, only one of the telemetry coils 60a-c is actually chosen as the coil to be used during telemetry. However, in other embodiments of the algorithm, more than one of the coils 60a-c might be chosen. For example, if coils 60a and 60c both exhibit suitable signal strength responses, each can be chosen as coils to be used during telemetry. In such a case, it would be preferable to cyclically activate each independently: first coil 60a, then coil 60c, then coil 60a again, etc. Or, both of the chosen coils 60a and 60c, if properly tuned, could be stimulated at the same time. This would of course require a switch 75 (FIGS. 10-11) which, in conjunction with switching signal 76, allows simultaneous connections between the microcontroller 70 and a plurality of the coils 60a-c. Such a scheme would mean that any given block of data is telemetered twice: once from coil 60a and once from 60c. While such redundancy might be time and energy inefficient, such redundancy may also be useful in improving the reliability of the data transfer and ease of use to the user.

Figure 15:
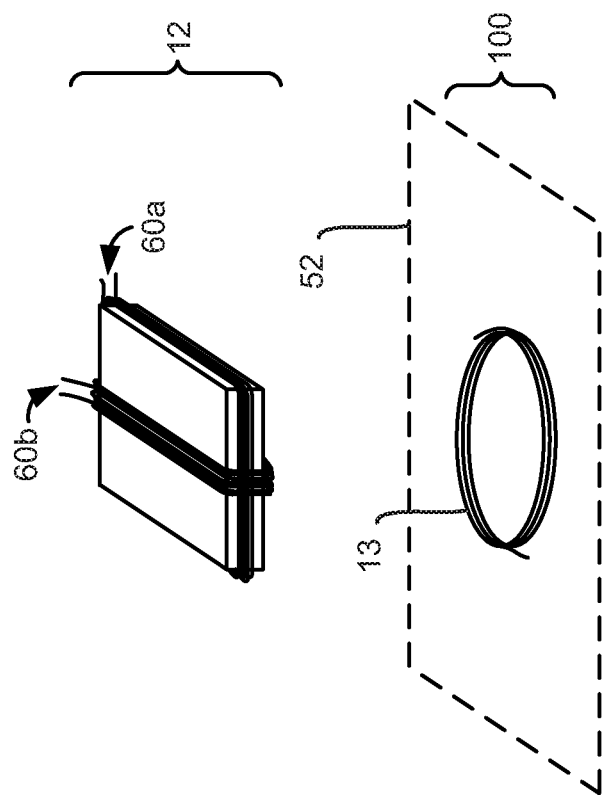
FIG. 15 shows an alternative embodiment of the invention in which only two orthogonal coils are used in the external controller.
Figure 14:
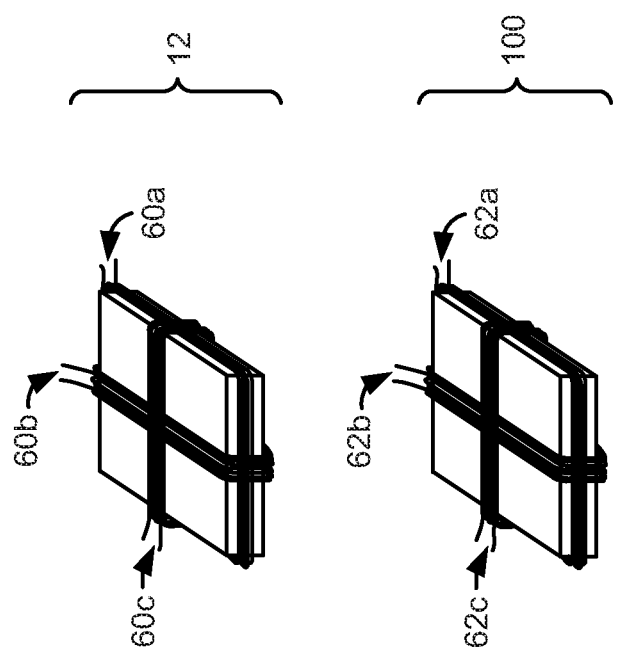
FIG. 14 shows an alternative embodiment of the invention in which three orthogonal telemetry coils are used in both the external controller and the IPG.

FIGS. 13-15 illustrate different but related ways of rendering the external controller 12 and IPG 100 orientation independent with respect to each other. For example, in FIG. 13, the coil 13 in the IPG 100 (see FIGS. 3-5) is replaced with orthogonal device coils 62a-c, while the external controller 12 retains its singular telemetry coil 17. From a field interaction standpoint, the configuration of FIG. 13 is not very different from the configuration of FIG. 6 in which the telemetry coils 60a-c in the external controller 12 are made orthogonal. Because of the orthogonal orientation of the three coils 62a-c in the IPG 100, stimulation of the external controller's coil 17 will induce a non-negligible current in at least one of the IPG's telemetry coils 62a-c. As is the case when the orthogonal coils are placed in the external controller (FIG. 6), the circuitry useable when the orthogonal coils 62a-c are within the IPG can be similar to those illustrated in FIG. 8-11, a point which recognizes that the coils are essentially similar whether they act as transmitters (e.g., in the external controller 12) or receivers (e.g., in the IPG 100).

Moreover, the algorithm for using the multiple orthogonal coils 62a-c in the IPG 100 can mimic either of the approaches of FIGS. 12A and 12B, although additional consideration is given to the fact that it is generally preferred in implantable technology to not continually energize the telemetry reception circuitry in the IPG 100, which might be wasteful of IPG power. Accordingly, the IPG 100 reception circuitry "wakes up" (i.e., is powered) only periodically (e.g., for 1 ms every second or so) to sense whether a significant amount of induced current has been received at one of the IPG's orthogonal telemetry coils 62a-c. Starting with a logical default device coil 62 (as described earlier), the received signal strength is assessed. If a suitable signal strength is received (i.e., above a given threshold), then that coil 62 can be chosen as the telemetry receiving coil, akin to the approach of FIG. 12B. Alternatively, the received signal strength can be assessed for all of the device coils 62a-c, with the coil with the highest signal strength being chosen by switch 75 as the coil for receiving telemetry, akin to the approach of FIG. 12A.

The embodiment of FIG. 13, in which the orthogonal device coils 62a-c are provided in the IPG 100 as opposed to the external controller 12, is certainly viable. However, it is preferred to use orthogonal coils in the external controller 12 (FIG. 6), instead of in the IPG 100 (FIG. 13). This is because space and power within the IPG 100 is typically limited, and the extra overhead of additional coils and additional electronics would generally militate that the orthogonal coils be placed in the external controller 12, where space and power consumption is less of a concern.

FIGS. 14 and 15 illustrate still further embodiments. In FIG. 14, both the external controller 12 and the IPG 100 contain three orthogonal telemetry coils 60a-c and 62a-c. Such a configuration allows for the highest signal strength combination of any of the coils 62a-c and of the coils 60a-c to be chosen for telemetry. Of course, this approach requires additional circuitry and algorithmic complexity.

FIG. 15 illustrates an embodiment in which only two orthogonal telemetry coils 60a and 60b are used. Such coils are shown in the external controller 12, but could also appear in the IPG 100 as explained earlier. In this embodiment, the provision of two orthogonal coils 60a and 60b increases the likelihood of an efficient orientation between the external controller 12 and the IPG 100 when compared with the single coil approaches of the prior art (see FIGS. 3-5), but requires less hardware and algorithmic complexity than when three orthogonal coils are used (FIGS. 6-13). Of course, using only two orthogonal coils 60a, 60b also reduces operational flexibility, because an orientation is possible which will result in negligible coupling between either of the telemetry coils 60a and 60b and IPG coil 13 (i.e., when the axis of the missing orthogonal coil is parallel to the axis of the IPG coil 13). But regardless, the provision of two orthogonal coils provides a wider range of acceptable external controller-to-IPG orientation profiles when compared with the single coil approach of the prior art.

While it is preferred that the multiple coils be orthogonal, it should be recognized that it is not strictly necessary for the multiple coils in either the external controller 12 (FIGS. 6-13) or the IPG 10 (FIG. 13) be at right angles to one another. Indeed, orientation freedom between the external controller 12 and the IPG 100 can be achieved even when the axes of the coils are not at right angles, but instead are at acute or obtuse angles with respect to each other, i.e., when the telemetry coils are wound around axes that are not parallel to each other. Moreover, recognizing that the axes of the coils can be arranged at angles other than 90-degrees, it should be apparent that more than three coils can be used. To cite one example exhibiting a natural symmetry, four telemetry coils could be arranged such that their axes have a tetrahedral orientation. Of course, such symmetry is not required, and the axes of the multiple coils could have other random angles with respect to each other.

Figure 1A:
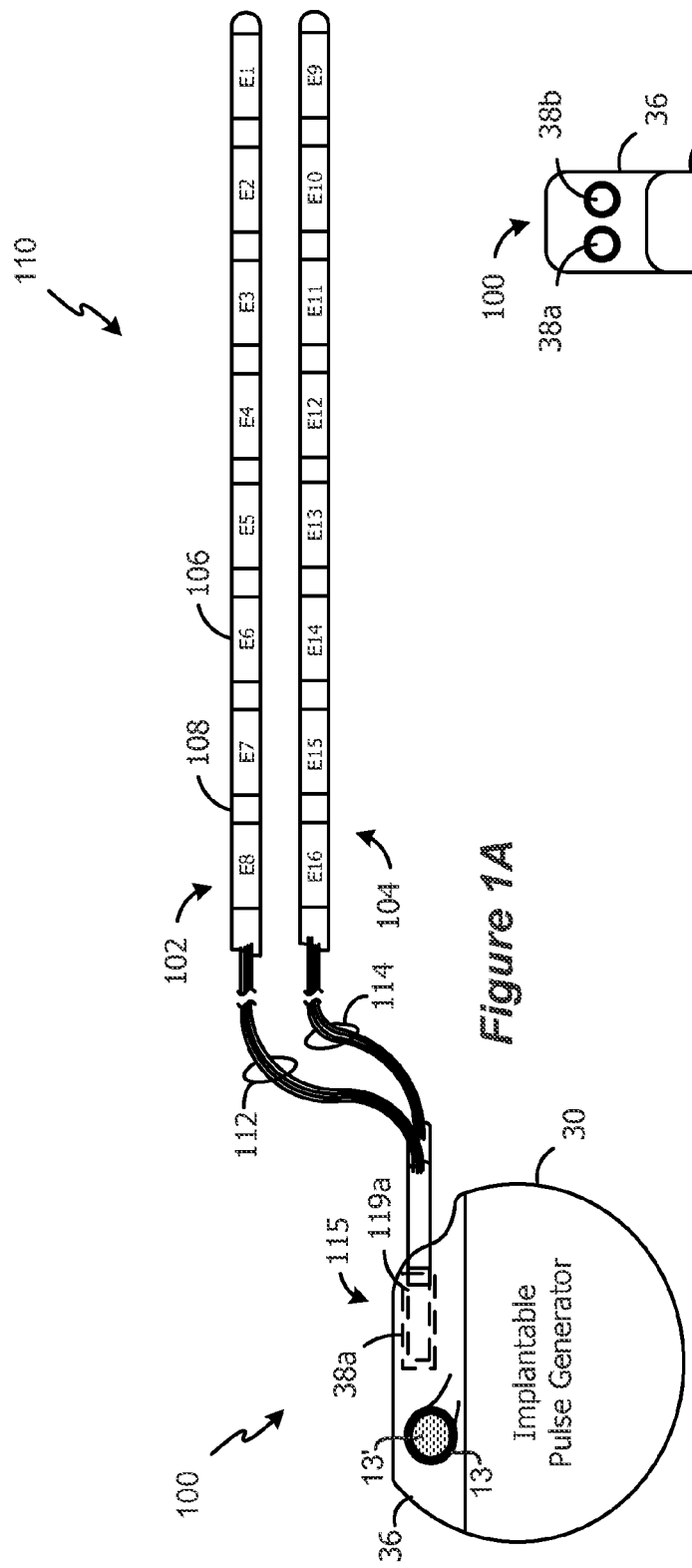
FIGS. 1A and 1B show an implantable pulse generator (IPG), and the manner in which an electrode array is coupled to the IPG in accordance with the prior art.
Figure 1B:
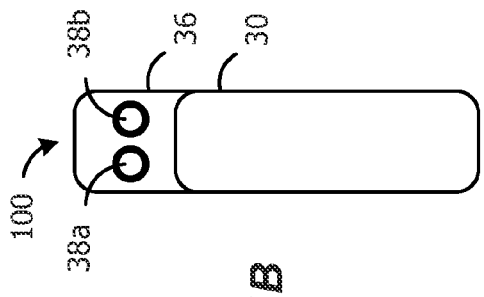
Figure 2:
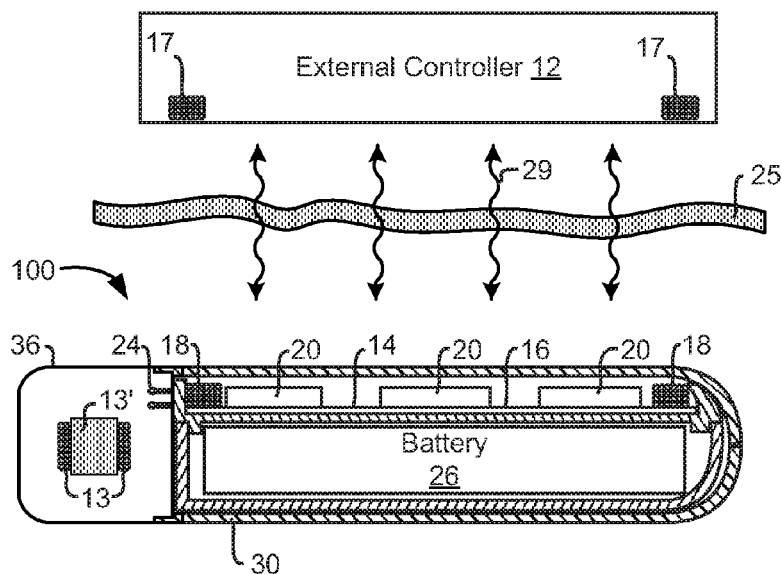
FIG. 2 shows a cross-sectional view of a prior art implantable pulse generator and an external controller.

It is preferred that the disclosed technique be used in the context of telemetry, i.e., with respect to those coils in either the external controller 12 or the IPG 100 that are involved in data transmission between the external controller 12 or the IPG 100. However, it should be noted that the disclosed techniques can also be used to improve induction between those coils involved in powering a RF powered IPG or in charging the battery 26 of a rechargeable IPG, 26 (see FIG. 2). As noted earlier, an IPG 100 typically contains a coil 18 (FIG. 2) for receiving induced energy from an external source (not shown), which may be integrated with the external controller 12 or may be another external device wholly discrete from the external controller 12. Proper orientation of the external device's coil with the coil 18 in the IPG can also be of concern, and therefore the use of orthogonal coils in either the external device or the IPG (but preferably in the external device) can benefit this aspect of IPG systems.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for communication or providing power from an external device having a plurality of coils to an implantable medical device, comprising:
    transmitting a signal via magnetic induction from a first of the plurality of coils and assessing receipt of the signal by the implantable medical device via magnetic induction at the first coil;
    repeating the above step for subsequent of the plurality of coils; and
    activating at least one coil to telemeter data or power to the implantable medical device via magnetic induction based upon the assessed receipt of the signals.

2. The method of claim 1, wherein the external device is sized to fit a user's hand.

3. The method of claim 1, wherein the plurality of coils are wound around axes that are orthogonal to each other.

4. The method of claim 1, wherein only one of the plurality of coils is activated to telemeter data or power to the implantable medical device via magnetic induction.

5. The method of claim 1, wherein activating at least one coil based upon the assessed receipt of the signals comprises assessing signal strengths of responses to the signals from the implantable medical device.

6. The method of claim 1, wherein the transmitting step and the repeating step comprises activating switching circuitry to couple each of the coils to transceiver circuitry.

7. The method of claim 1, wherein a transceiver circuit is coupled to each of the coils, and wherein the transmitting step and the repeating step comprises activating switching circuitry to couple each of the transceiver circuitry to controller circuitry.

8. A method for communication or providing power from an external device having a plurality of coils to an implantable medical device, comprising:
    transmitting a first signal via magnetic induction from a first of the plurality of coils;
    if the first signal is satisfactorily received at the implantable medical device, activating the first coil to telemeter data or power to the implantable medical device via magnetic induction;
    if the first signal is not satisfactorily received, transmitting a second signal via magnetic induction from a second of the plurality of coils; and
    if the second signal is satisfactorily received at the implantable medical device, activating the second coil to telemeter data or power to the implantable medical device via magnetic induction.

9. The method of claim 8, further comprising:
    if the second signal is not satisfactorily received at the implantable medical device, transmitting a third signal via magnetic induction from a third of the plurality of coils; and
    if the third signal is satisfactorily received at the implantable medical device, activating the third coil to telemeter data or power to the implantable medical device via magnetic induction.

10. The method of claim 8, wherein the external device is sized to fit a user's hand.

11. The method of claim 8, wherein the plurality of coils are wound around axes that are orthogonal to each other.

12. The method of claim 8, wherein if the first or second signal is satisfactorily received at the implantable medical device is determined by assessing a signal strength of a response to the first or second signal.

13. The method of claim 8, wherein activating the first or second coils comprises activating switching circuitry to couple the first or second coils to transceiver circuitry.

14. The method of claim 8, wherein a transceiver circuit is coupled to each of the first and second coils, and wherein activating the first or second coils comprises activating switching circuitry to couple each of the transceiver circuitry to controller circuitry.

15. The method of claim 8, further comprising storing in the external device historical data regarding which of the plurality of coils have been activated in the past.

16. The method of claim 15, wherein the first coil is chosen using the historical data.

17. The method of claim 16, wherein the second coil is also chosen using the historical data.

* * * * *